US009629603B2

(12) United States Patent
Enomoto

(10) Patent No.: US 9,629,603 B2
(45) Date of Patent: *Apr. 25, 2017

(54) RADIOGRAPHIC IMAGING DEVICE, RADIOGRAPHIC IMAGING SYSTEM, COMPUTER-READABLE MEDIUM STORING RADIOGRAPHIC IMAGING PROGRAM, AND RADIOGRAPHIC IMAGING METHOD

(71) Applicant: FUJIFILM CORPORATION, Minato-ku, Tokyo (JP)

(72) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/093,995

(22) Filed: Apr. 8, 2016

(65) Prior Publication Data
US 2016/0220220 A1 Aug. 4, 2016

Related U.S. Application Data

(63) Continuation of application No. 14/606,005, filed on Jan. 26, 2015, now Pat. No. 9,332,956, which is a (Continued)

(30) Foreign Application Priority Data

Oct. 19, 2010 (JP) .................... 2010-234578

(51) Int. Cl.
*A61B 6/00* (2006.01)
*H05G 1/28* (2006.01)
(Continued)

(52) U.S. Cl.
CPC ............ *A61B 6/548* (2013.01); *A61B 6/5258* (2013.01); *A61B 6/542* (2013.01); *G06T 7/0002* (2013.01);
(Continued)

(58) Field of Classification Search
CPC .......... A61B 6/52; A61B 6/5294; A61B 6/54; A61B 6/542; H05G 1/08; H05G 1/28; H05G 1/38; H05G 1/44; H05G 1/46
See application file for complete search history.

(56) References Cited

U.S. PATENT DOCUMENTS 7,822,178 B2 * 10/2010 Enomoto ............. A61B 6/00
378/207
8,270,566 B2 9/2012 McNabb
(Continued)

FOREIGN PATENT DOCUMENTS

JP 2004-024682 A 1/2004
JP 2004-056566 A 2/2004
(Continued)

OTHER PUBLICATIONS

Japanese Office Action dated Oct. 23, 2012, issued for the Japanese Patent Application No. 2010-234578.
(Continued)

*Primary Examiner* — Thomas R Artman
(74) *Attorney, Agent, or Firm* — SOLARIS Intellectual Property Group, PLLC

(57) ABSTRACT

The present invention provides a radiographic imaging device including: a detecting section that detects a dose of radiation that has been irradiated when imaging a radiographic image corresponding to irradiated radiation; and a determining section that determines whether the radiographic image is a valid image on the basis of the dose of radiation that has been detected by the detecting section.

13 Claims, 6 Drawing Sheets

Related U.S. Application Data continuation of application No. 13/274,366, filed on Oct. 17, 2011, now Pat. No. 8,958,529.

(51) Int. Cl.
  *H04N 5/32* (2006.01)
  *G06T 7/00* (2017.01)
  *H04N 5/225* (2006.01)
  *H04N 5/232* (2006.01)

(52) U.S. Cl.
  CPC ............... *H04N 5/32* (2013.01); *H05G 1/28* (2013.01); *G06T 2207/10116* (2013.01); *G06T 2207/30168* (2013.01); *H04N 5/2258* (2013.01); *H04N 5/232* (2013.01)

(56) References Cited

U.S. PATENT DOCUMENTS

| | | | |
|---|---|---|---|
| 8,958,529 | B2 | 2/2015 | Enomoto |
| 9,332,956 | B2* | 5/2016 | Enomoto ............... H04N 5/32 |
| 2009/0016490 | A1 | 1/2009 | Campbell |
| 2010/0040199 | A1* | 2/2010 | Enomoto ............... A61B 6/00 378/98.12 |
| 2010/0102241 | A1 | 4/2010 | Zeller |
| 2012/0093291 | A1 | 4/2012 | Enomoto |
| 2012/0119099 | A1 | 5/2012 | Zeller |
| 2012/0128116 | A1 | 5/2012 | Sabol |
| 2015/0139399 | A1* | 5/2015 | Enomoto ............... H04N 5/32 378/62 |
| 2016/0220220 | A1* | 8/2016 | Enomoto ............... H04N 5/32 |

FOREIGN PATENT DOCUMENTS

| | | |
|---|---|---|
| JP | 2004-065635 A | 3/2004 |
| JP | 2005-204960 A | 8/2005 |
| JP | 2006-42967 A | 2/2006 |
| JP | 2006-81735 A | 3/2006 |
| JP | 2006-122115 A | 5/2006 |
| JP | 2010-121944 A | 6/2010 |
| JP | 2010-214056 A | 9/2010 |
| JP | 2010-217141 A | 9/2010 |
| WO | 2004008965 A1 | 1/2004 |

OTHER PUBLICATIONS

Chinese Office Action dated Sep. 16, 2014, issued for the Chinese Patent Application No. 201110317000.0.
Extended European Search Report dated Sep. 19, 2012, issued for the European Patent Application No. 11185519.3.
Japanese Office Action dated Feb. 17, 2015, issued for the Japanese Patent Application No. 2014-106243.
European Office Action dated Mar. 5, 2015, issued for the European Patent Application No. 11185519.3.
U.S. Office Action dated Sep. 30, 2015, issued for the U.S. Appl. No. 14/606,005.
English language translation of the following: Office action dated Sep. 20, 2016 from the JPO in a Japanese patent application No. 2015-200500 corresponding to the instant patent application.
Summons to attend oral proceedings pursuant to Rule 115(1) EPC dated Nov. 22, 2016, issued in corresponding EP Patent Application.

* cited by examiner

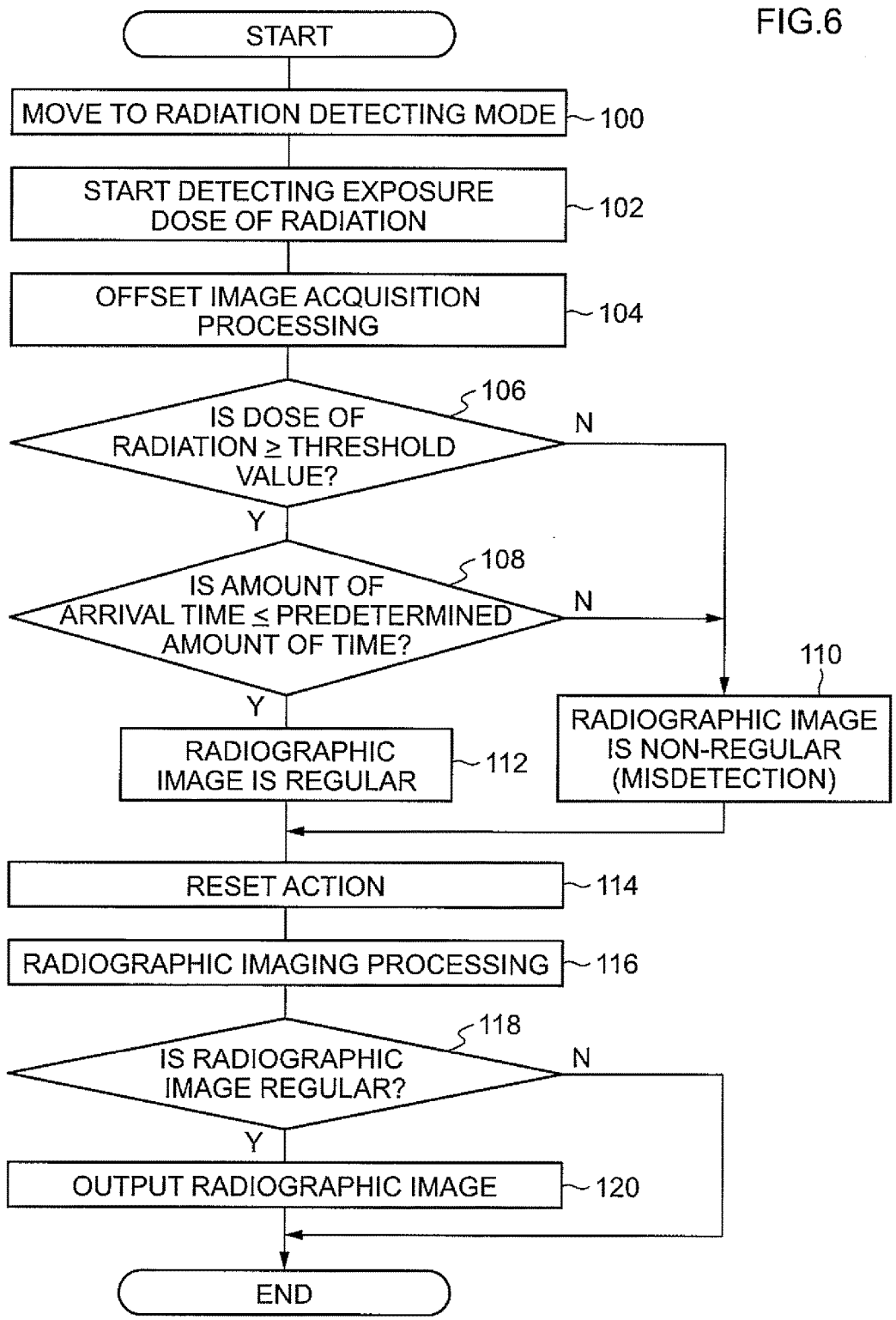

RADIOGRAPHIC IMAGING DEVICE, RADIOGRAPHIC IMAGING SYSTEM, COMPUTER-READABLE MEDIUM STORING RADIOGRAPHIC IMAGING PROGRAM, AND RADIOGRAPHIC IMAGING METHOD

CROSS-REFERENCE TO RELATED APPLICATION

This application is a continuation application of, and claims domestic priority to, U.S. patent application Ser. No. 14/606,005 filed Jan. 26, 2015, which is a continuation application of, and claims domestic priority to, U.S. patent application Ser. No. 13/274,366 filed Oct. 17, 2011, which claims priority under 35 USC 119 from Japanese Patent Application No. 2010-234578 filed on Oct. 19, 2010. The present continuation application hereby incorporates by reference all documents referenced above.

BACKGROUND OF THE INVENTION

Field of the Invention

The present invention relates to a radiographic imaging device, a radiographic imaging system, a computer-readable medium storing a radiographic imaging program, and a radiographic imaging method. The present invention particularly relates to a radiographic imaging device, a radiographic imaging system, a computer-readable medium storing a radiographic imaging program, and a radiographic imaging method, that images a radiographic image without having to synchronize with a radiation irradiation operation of a radiation generation device.

Description of the Related Art

Conventional radiographic imaging systems that perform radiographic imaging for medical diagnoses purpose have been known. As such radiographic imaging system, there is a radiographic imaging system including a radiation generation device, a radiation detection device, and a control device. The radiation generation device generates radiation. The radiation detection device is a cassette or the like, that serves as a radiographic imaging device that detects the radiation that has passed through a subject to image a radiographic image. The control device controls the radiation generation device and the radiation detection device.

In the radiation detection device, a conventional technology that performs an image analysis of the imaged radiographic image, determines whether a subject image is being properly imaged, and outputs the determination result to an external device, has been known. This technology informs a user, with the output, whether the imaging is valid (see Japanese Patent Application Laid-Open (JP-A) No. 2006-122115, JP-A No. 2006-42967, and JP-A No. 2006-81735).

Further, there is a radiographic imaging system including a radiation detection device that images a radiographic image without receiving an instruction from the control device, and without having to synchronize with the irradiation operation in which the radiation generation device irradiates the radiation. In this radiographic imaging system, there are cases where, even when the radiation detection device does not have to image a radiographic image, the radiation detection device detects the irradiated radiation, images a radiographic image, and outputs the imaged radiographic image to the control device or the like.

For example, in a conventional radiographic imaging system equipped with plural radiation detection devices, such as a radiation detection device for imaging in a standing position and a radiation detection device for imaging in a lying position, the radiation detection devices detect irradiation of the radiation and perform an imaging operation without having to connect to the control device and the radiation generation device. Accordingly, in a conventional radiographic imaging system, there are cases where, as a result of the radiation being irradiated, not only the radiation detection device that is to image a radiographic image but also the radiation detection device that does not have to image a radiographic image may perform imaging operation, and a false radiographic image (miss-detecting the radiation) may be imaged. In such cases, when the plural radiation detection devices sequentially output to the control device the imaged radiographic images, a false radiographic image may also be outputted to the control device.

SUMMARY OF THE INVENTION

The present invention provides a radiographic imaging device, a radiographic imaging system, a radiographic imaging program, and a radiographic imaging method that prevent the output of a false radiographic image from a radiographic imaging device that images a radiographic image.

A first aspect of the present invention is a radiographic imaging device including: a detecting section that detects a dose of radiation that has been irradiated when imaging a radiographic image corresponding to irradiated radiation; and a determining section that determines whether the imaged radiographic image is a valid image on the basis of the dose of radiation that has been detected by the detecting section.

The determining section of the first aspect of the present invention determines whether or not the radiographic image is a valid image on the basis of the dose of radiation detected by the detecting section. Accordingly, the first aspect of the present invention may prevent output of a false radiographic image.

In a radiographic imaging device, a radiographic image that is not a valid image (false radiographic image) may be imaged. For example, a case in which a radiographic imaging device detects the radiation that has been irradiated with respect to another radiographic imaging device, and may image a false radiographic image. In the present invention, the radiographic imaging device determines whether the radiographic image is a valid image, in order to prevent output of a false radiographic image that is not valid, from the radiographic imaging device. When a false radiographic image has been outputted, the processing speed on the receiving side the false radiographic image may drop. In the present invention, a false radiographic image is prevented from being outputted, and therefore a drop in processing speed may be suppressed.

In a second aspect of the present invention, in the first aspect, may further include, an output section that outputs the radiographic image that has been imaged, and a control section that controls the output section not to output the radiographic image in a case in which the determining section determines that the radiographic image is not a valid image.

In the second aspect of the present invention, the control section controls the output section not to output the radiographic image when it has been determined that the radiographic image is not a valid image by the determining section. Accordingly, the second aspect of the present invention may prevent a false radiographic image from being outputted.

In a third aspect of the present invention, in the first aspect or the second aspect, the determining section may determine that the radiographic image is not a valid image when the dose of radiation, detected by the detecting section, does not exceed a predetermined threshold value.

The third aspect of the present invention determines that the radiographic image is not a valid image when the dose of radiation detected by the detecting section does not exceed the predetermined threshold value, that is, when the detected dose of radiation is small.

In a fourth aspect of the present invention, in the first aspect to the third aspects, the determining section may determine that the radiographic image is not a valid image when a period until the dose of radiation, detected by the detecting section, reaches a predetermined threshold value exceeds a predetermined period.

The fourth aspect of the present invention determines that the radiographic image is not a valid image when, even when the dose of radiation detected by the detection section has exceeded the predetermined threshold value, the period until the dose of radiation reaches the threshold value exceeds the predetermined period (Namely, a case where the detected dose of radiation per unit of time is small).

In a fifth aspect of the present invention, in the first aspect to the fourth aspects, the determining section may determine whether the radiographic image is a valid image on the basis of the dose of radiation, detected by detecting section, at the time when acquiring a correction image for correcting the radiographic image.

A sixth aspect of the present invention is a radiographic imaging system including: a control device that instructs settings relating to imaging a radiographic image; a radiation irradiation device that irradiates radiation on the basis of an instruction from the control device; and the radiographic imaging device according to any one of first to fifth aspects which, without having to synchronizing with the operation of irradiation of the radiation by the radiation irradiation device, images a radiographic image corresponding to the radiation that has been irradiated from the radiation irradiation device, and outputs the imaged radiographic image to the control device.

In a seventh aspect of the present invention, in the sixth aspect, the radiographic imaging system may include a plurality of the radiographic imaging device according to any one of first to fifth aspects.

An eighth aspect of the present invention is a radiographic imaging method including: detecting a dose of radiation that has been irradiated when imaging a radiographic image corresponding to irradiated radiation; and determining whether the imaged radiographic image is a valid image on the basis of the detected dose of radiation.

A ninth aspect of the present invention is a computer-readable medium in which is recorded a radiographic imaging program for causing a computer to execute radiographic imaging process, the process including: determining whether a imaged radiographic image is a valid image on the basis of a dose of radiation that has been detected by a detecting section that detects a dose of radiation that has been irradiated when imaging the radiographic image corresponding to irradiated radiation.

Accordingly, the above-described aspects of the present invention may prevent output of a false radiographic image from a radiographic imaging device that images a radiographic image.

BRIEF DESCRIPTION OF THE DRAWINGS

Exemplary embodiment of the present invention will be described in detail based on the following figures, wherein:

FIG. 6 is a flowchart showing an example of a flow of false image output suppression processing that is executed in the radiation detection device according to the exemplary embodiment.

DETAILED DESCRIPTION

Figure 1:
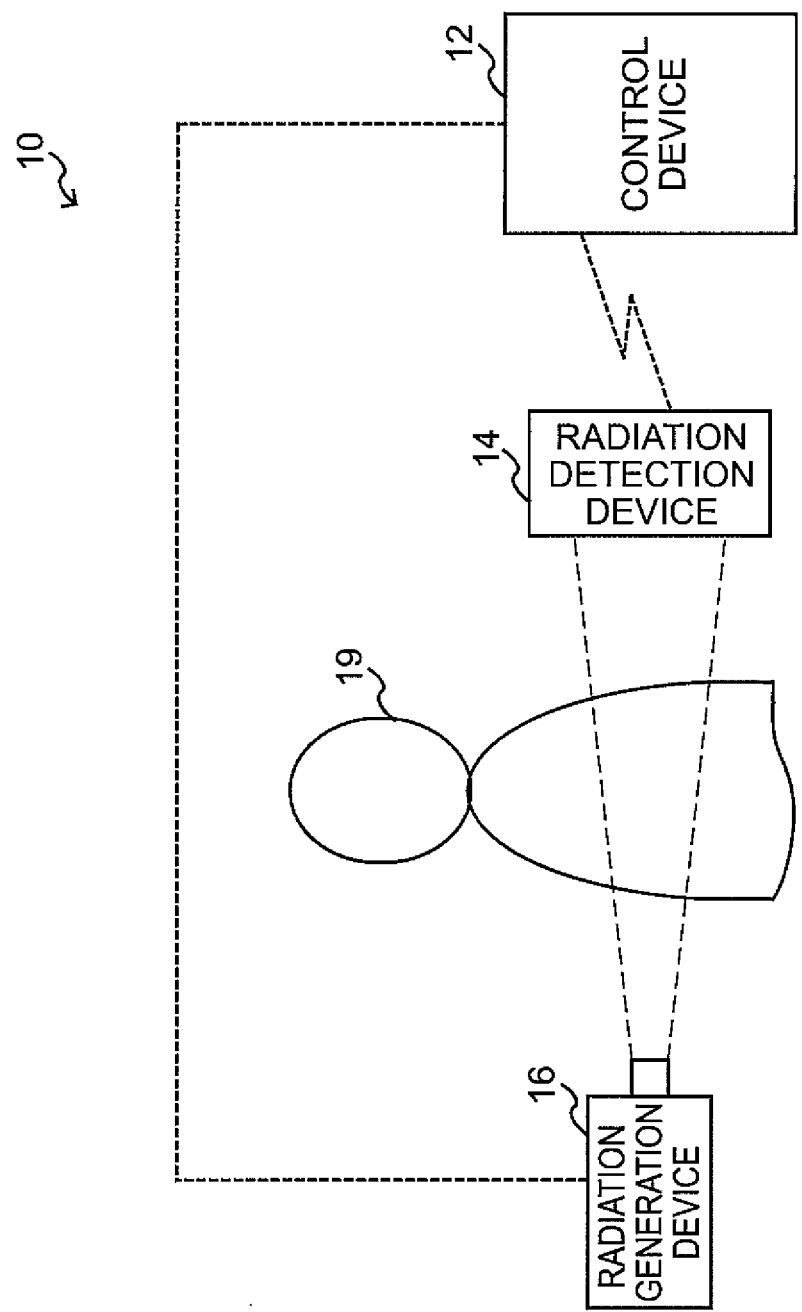
FIG. 1 is a diagram showing an example configuration of a radiographic imaging system according to the exemplary embodiment.
Figure 2:
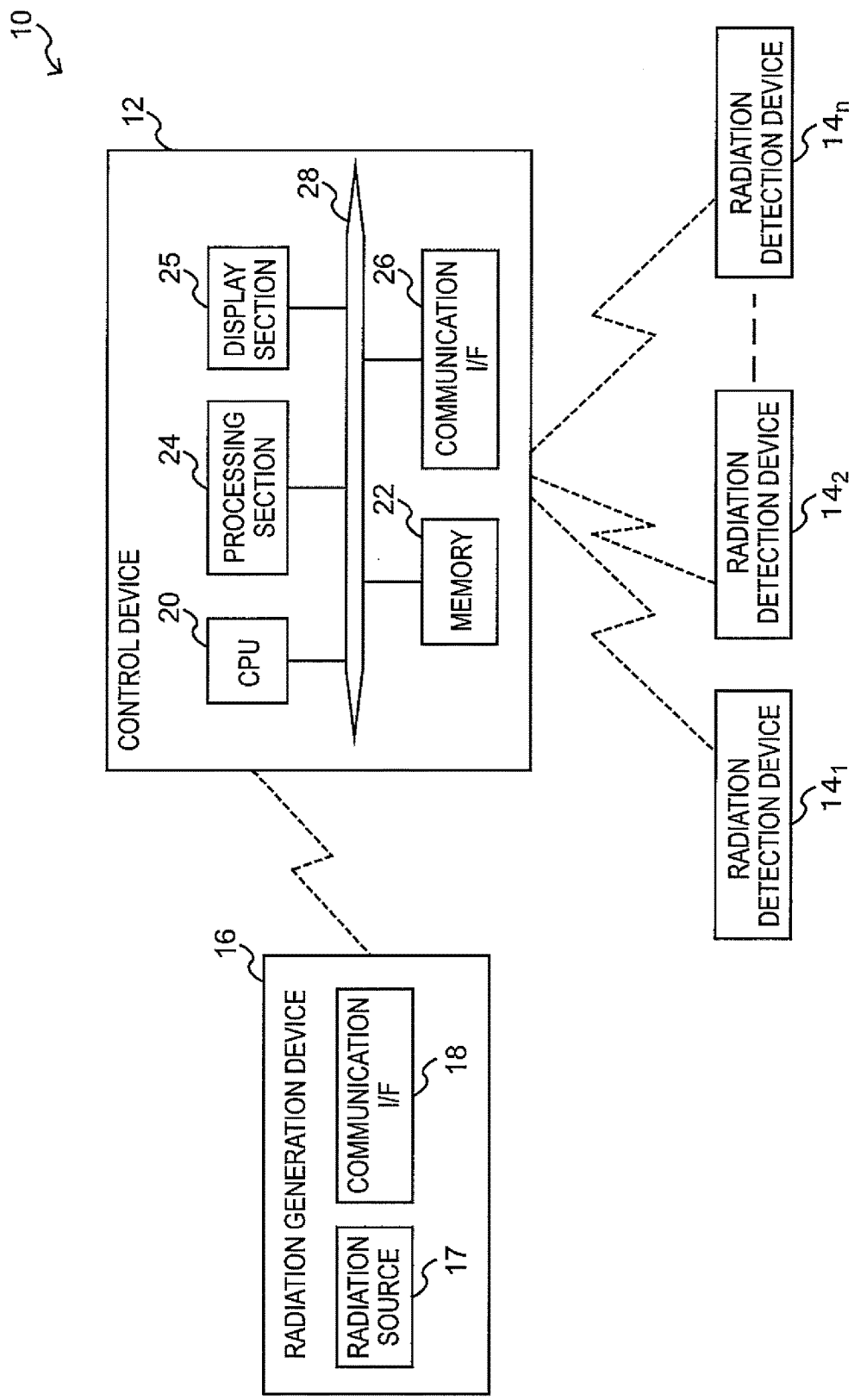
FIG. 2 is diagram showing an example configuration of the radiographic imaging system according to the exemplary embodiment shown in FIG. 1.

Exemplary embodiment of the present invention will be described below with reference to the drawings. FIG. 1 and FIG. 2 show the configuration of a radiographic imaging system 10 of the present exemplary embodiment. The radiographic imaging system 10 includes, a radiation generation device 16 that irradiates radiation (e.g., X-rays) to a subject 19, a radiation detection device 14 that detects the radiation that has been irradiated from the radiation generation device 16 and has passed through the subject 19, and a control device (console) 12 that instructs the imaging of the radiographic image, acquires image information from the radiation detection device 14, and performs various types of processing. The radiation that carries image information as a result of being irradiated from the radiation generation device 16 and passing through the subject 19, positioned in an imaging position, is irradiated to the radiation detection device 14.

As shown in FIG. 2, the radiographic imaging system 10 of the present exemplary embodiment includes more than one (in FIG. 2, n number) radiation detection devices 14 ($14_1$ to $14_n$). In the description below, subscript symbols (1 to n) for distinguishing between the individual radiation detection devices 14 will be added after the number "14" when distinguishing between the individual radiation detection devices 14. On the other hand, subscript symbols (1 to n) will be omitted in the case of generically referring to the radiation detection devices 14 without distinguishing between thereof.

The control device 12 is wirelessly connected to the radiation detection devices 14, and executes various types of controls with respect to the radiation detection devices 14 by wirelessly transmitting commands and data via a communication interface (I/F) 26. The control device 12 is also wirelessly connected to the radiation generation device 16, and has controls the timing for the radiation generation device 16 to irradiate the radiation (e.g., X-rays). The control device 12 is configured to include a central processing section (CPU) 20, a memory 22, a processing section 24, a display section 25, and the communication I/F 26. The CPU 20, the memory 22, the processing section 24, the display section 25, and the communication I/F 26 are interconnected by a bus 28, such as a CPU bus, that sends signals to and receives signals from each other. The CPU 20 has the function of controlling the operations of the entire control device 12 by executing various types of programs that are pre-stored in the memory 22. The processing section 24 acquires image data from the radiation detection devices 14 and performs various types of processing. The display section 25 displays, for example, radiographic images received via the communication I/F 26 from the radiation detection devices 14.

The radiation generation device 16 is configured to include a radiation source 17 and a communication interface (I/F) 18. The radiation generation device 16 is wirelessly connected to the control device 12 via the communication I/F 18, and irradiates the radiation from the radiation source 17 to the subject 19, at a timing based on the control of the control device 12.

The radiographic imaging system 10 of the present exemplary embodiment includes more than one of the radiation detection devices 14. As an example of the radiographic imaging system 10 including more than one of the radiation detection devices 14, the radiation detection devices 14 may be provided in accordance with the imaging purpose of the radiographic imaging system 10, such as for imaging in a standing position, for imaging in a lying position, and for front imaging and side imaging of the subject 19. Further, as an example of the radiographic imaging system 10 including more than one of the radiation detection devices 14, the radiation detection devices 14 may be provided along the body height direction of the subject 19 for long-length imaging. However, the radiographic imaging system 10 of the present invention is not limited to thereto. The types and so forth of the plural radiation detection devices 14 are not particularly limited.

Figure 3:
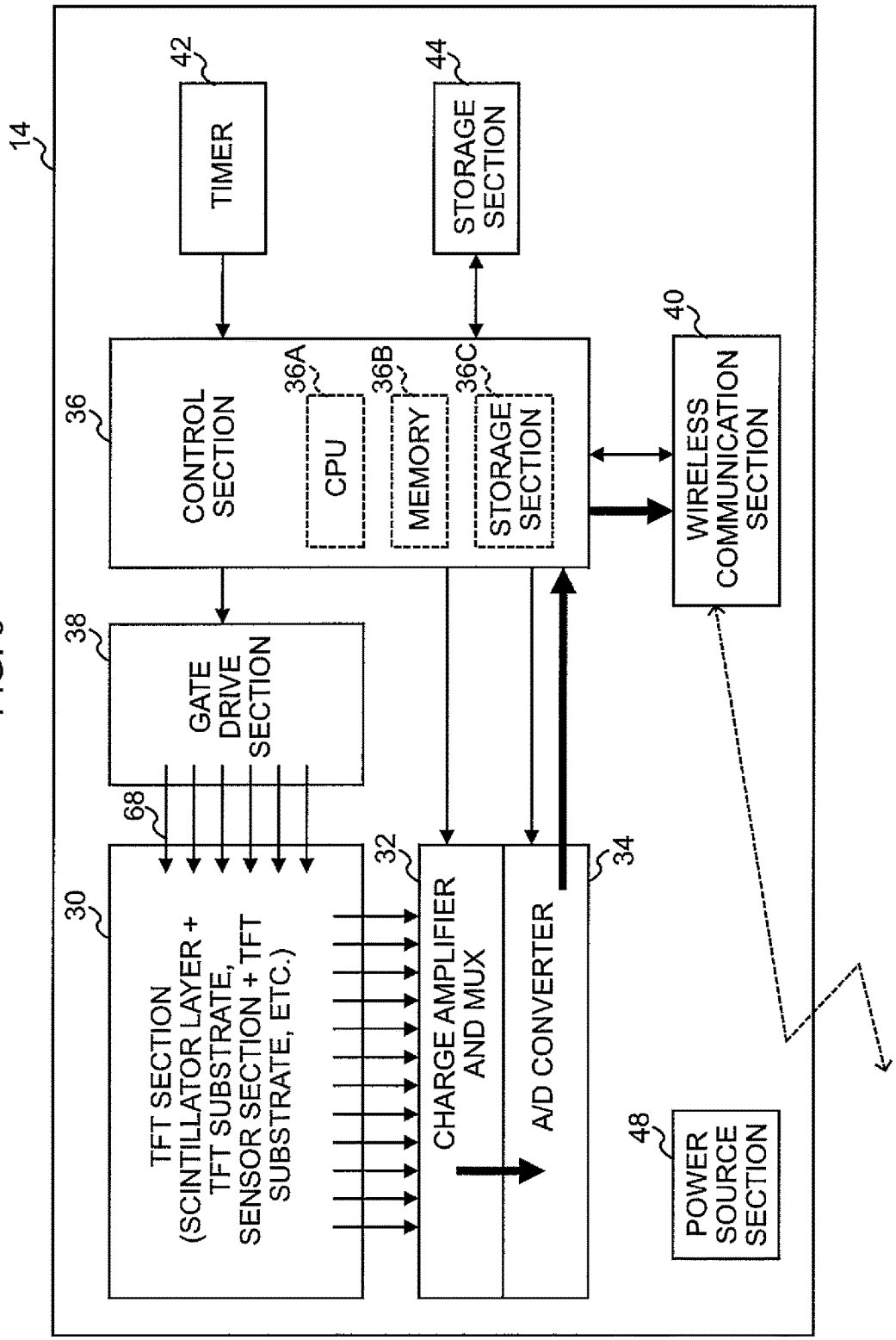
FIG. 3 is a functional block diagram showing an example configuration of a radiation detection device according to the exemplary embodiment.

FIG. 3 is a functional block diagram showing an example configuration of the radiation detection devices 14 of the present exemplary embodiment. Note that each of the radiation detection devices 14 of the present exemplary embodiment is a radiation detection panel unit, such as flat panel detection devices (FPD) that are known as cassettes.

Each of the radiation detection devices 14 is configured to include a thin-film transistor (TFT) section 30, a charge amplifier and multiplexer (MUX) 32, an analog-to-digital (A/D) converter 34, a control section 36, a gate drive section 38, a wireless communication section 40, a timer 42, a storage section 44, and a power source section 48.

Figure 4:
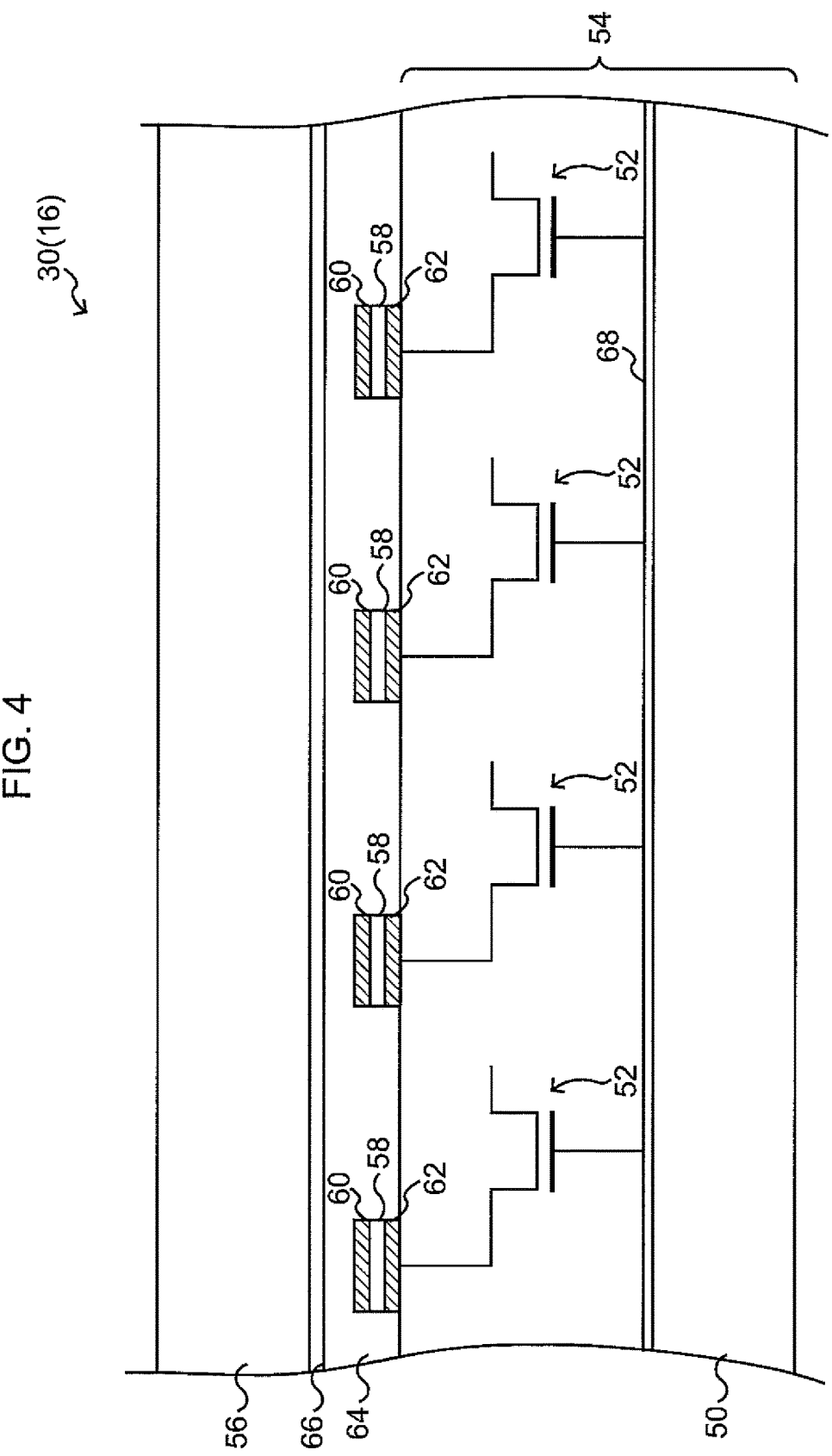
FIG. 4 is a cross-sectional view showing an example configuration of a TFT section of the radiation detection device according to the exemplary embodiment.

The TFT section 30 detects the irradiated radiation. FIG. 4 is a cross-sectional view showing an example configuration of the TFT section 30. As shown in FIG. 4, the TFT section 30 is configured to include a TFT substrate 54 in which switch elements 52 such as TFTs are formed on an insulating substrate 50.

The switch elements 52 are connected to gate lines 68 for switching ON and OFF the switch elements 52. A scintillator layer 56 that converts the irradiated radiation made incident thereon into light is formed on the TFT substrate 54. The scintillator layer 56, for example, may be formed by using a CSI:Tl or Gos ($Gd_2O_2S$:Tb) phosphor or the like. However, the materials of the scintillator layer 56 are not limited to thereto.

As the insulating substrate 50, for example, a glass substrate, various types of ceramic substrates, a resin substrate, or the like can be used. However, materials of the insulating substrate 50 are not limited to thereto.

Photoconductive layers 58, that generate charges when the light into which the radiation has been converted by the scintillator layer 56 is illuminated, are placed between the scintillator layer 56 and the TFT substrate 54. Bias electrodes 60 for applying a bias voltage to the photoconductive layers 58 are disposed on the surfaces of the photoconductive layers 58 on the scintillator layer 56 side.

Charge collecting electrodes 62 for collecting the charges generated by the photoconductive layers 58 are disposed on the TFT substrate 54. In the TFT substrate 54, the charges collected by the charge collecting electrodes 62 are read out by the switch elements 52.

The charge collecting electrodes 62 are arranged in a matrix (two-dimensionally) on the TFT substrate 54. In correspondence thereto, the switch elements 52 are arranged in a matrix on the insulating substrate 50. A flattening (leveling) layer 64 for flattening the top of the TFT substrate 54 is formed on the TFT substrate 54. Between the TFT substrate 54 and the scintillator layer 56, an adhesive layer 66 for adhering the scintillator layer 56 to the TFT substrate 54 is formed on the flattening layer 64.

To the radiation detection device 14, the radiation may be irradiated from the front side on which the scintillator layer 56 is adhered (so that the front side becomes the imaging surface) or may be irradiated to the radiation detection device 14 from the TFT substrate 54 side (back side) (so that the back side becomes the imaging surface). In the case where the radiation is irradiated to the radiation detection device 14 from the front side, the upper surface side (the opposite side of the TFT substrate 54 side) of the scintillator layer 56 emits light more strongly. In the case where the radiation is irradiated to the radiation detection device 14 from the back side, the radiation that has passed through the TFT substrate 54 is irradiated on the scintillator layer 56, and the TFT substrate 54 side of the scintillator layer 56 emits light more strongly. Charges are generated in the photoconductive layers 58 by the light that has been converted from radiation and illuminated by the scintillator layer 56. Accordingly, the sensitivity of the radiation detection device 14 with respect to the radiation may be set higher in the case where the radiation is irradiated from the front side, than in the case where the radiation is irradiated from the back side. This is due to that the radiation does not pass through the TFT substrate 54 in the case where the radiation is irradiated from the front side. On the other hand, the resolution of the radiographic image obtained by the imaging may be made higher in the case where the radiation is irradiated from the back side than in the case where the radiation is irradiated from the front side. This is due to that the light emission position of the scintillator layer 56 with respect to the photoconductive layers 58 is closer in the case where the radiation is irradiated from the back side.

Figure 5:
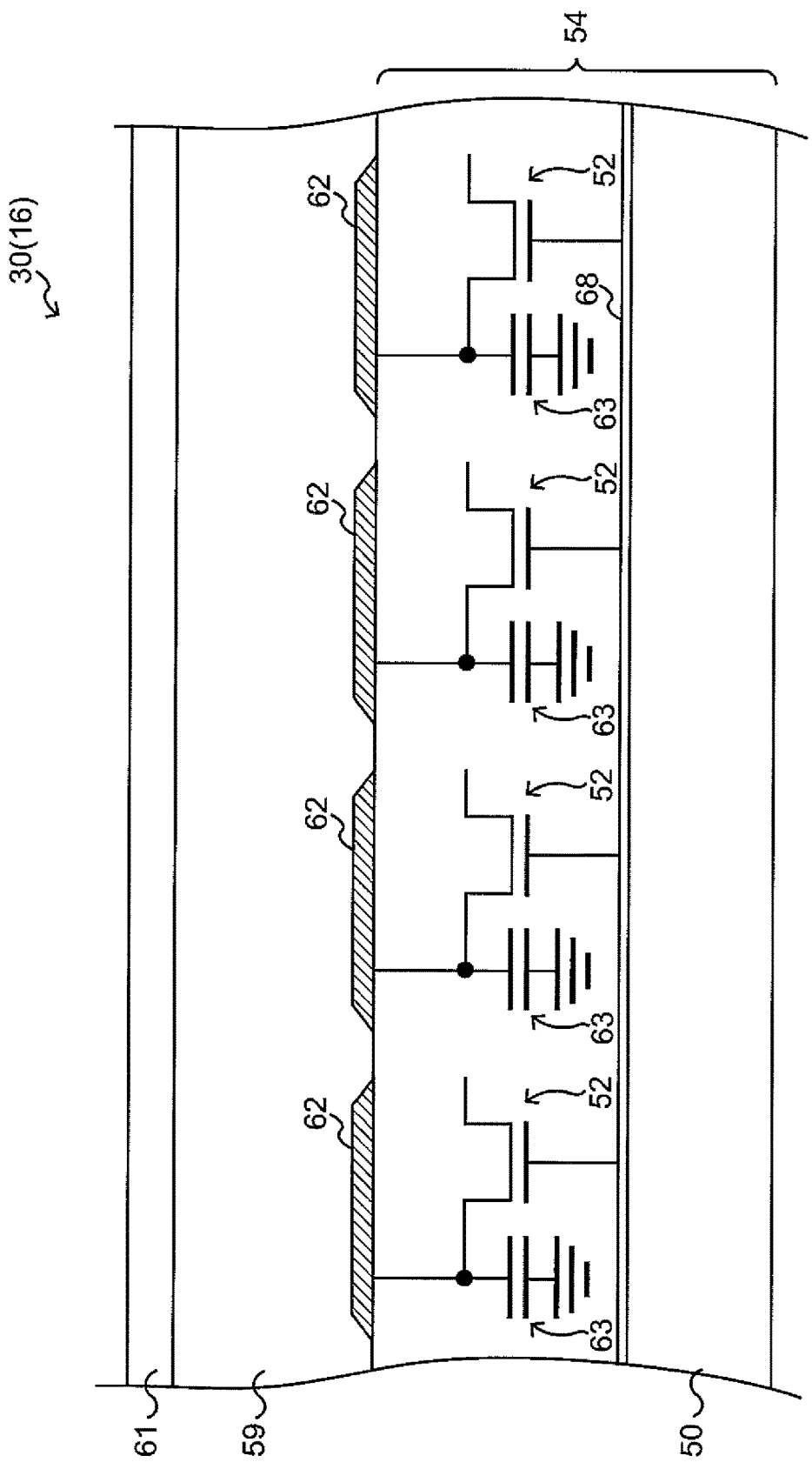
FIG. 5 is a cross-sectional view showing an example an alternative configuration of the TFT section of the radiation detection device according to the exemplary embodiment.

The configuration of the TFT section 30 is not limited to the above. The TFT section 30 may take alternative configuration as long as it has the function of accumulating and outputting charges corresponding to the radiation that has been irradiated to the radiation detection device 14. FIG. 5 shows an example of alternative configuration of the TFT section 30. FIG. 5 is a cross-sectional view showing an example of an alternative configuration of the TFT section 30. The TFT section 30 shown in FIG. 5 employs a direct-conversion-type configuration that directly converts radiation into charges, with a sensor section using amorphous selenium or the like, and accumulates the charges.

In the TFT section 30 shown in FIG. 5, as an example of a radiation conversion layer that converts the irradiated radiation, a photoconductive layer 59 that converts the irradiated radiation into charges is formed on the TFT substrate 54. As the photoconductive layer 59, a compound or the like whose main component is at least one of amorphous selenium (a-Se), $Bi_{12}MO_{20}$ (M: Ti, Si, Ge), $Bi_4M_3O_{12}$ (M: Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs, etc., is used. However, an amorphous material, whose dark resistance is high, which exhibits excellent photoconductivity with respect to radiation irradiation, and is capable of being formed in a large area at a low temperature by vacuum deposition, is preferred.

On the photoconductive layer 59 at the front surface side, a bias electrode 61 for applying a bias voltage to the photoconductive layer 59 is formed.

In the direct-conversion-type TFT section 30, like the indirect-conversion-type TFT section 30 (see FIG. 4), the charge collecting electrodes 62 that collect the charges generated by the photoconductive layer 59 are formed on the TFT substrate 54.

The TFT substrate 54 in the direct-conversion-type TFT section 30 is equipped with charge storage capacitors 63 that accumulate the charges collected by the charge collecting electrodes 62. The charges accumulated in the charge storage capacitors 63 are read out by the switch elements 52.

The charges that have been read out in the TFT section 30 are outputted to the charge amplifier and MUX 32 as electrical signals. The charge amplifier 32 amplifies the electrical signals and converts the amplified electrical signals into analog voltages. As a specific example, the charge amplifier 32 is configured by an amplification circuit and a sample-and-hold circuit using op-amps and capacitors. The electrical signals held in the sample-and-hold circuit are configured to undergo parallel-to-serial conversion in the MUX 32 and be outputted to the A/D converter 34.

The A/D converter 34 converts the serially inputted analog voltages into digital signals that are easier to handle. The two-dimensional image data of the radiographic image converted into the digital signals by the A/D converter 34 are outputted to the control section 36. In the present exemplary embodiment, an image memory (not shown) is connected to the A/D converter 34, and the transmitted image data are stored in sequence in the image memory. In the present exemplary embodiment, the image memory has a storage capacity capable of storing a predetermined number of frames of image data, and the image memory is configured that each time the imaging of a radiographic image is performed, the image data obtained by the imaging are sequentially stored in the image memory.

The control section 36 is configured by a microcomputer, is configured to include a CPU 36A, a memory 36B including a ROM and a RAM, and a nonvolatile storage section 36C including a flash memory or the like, and controls the operations of the entire radiation detection device 14 by executing, with the CPU 36A, various types of programs stored in the memory 36B. In the present exemplary embodiment, the control device 36 also has the function of determining, in accordance with the dose of radiation to which the radiation detection device 14 has been irradiated, whether the radiographic image that has been imaged is a valid image and, when the radiographic image is not a valid image (a false image), controlling the wireless communication section 40 to not output the radiographic image to the control device 12 (details described below).

Further, the image data are transmitted to the wireless communication section 40. The wireless communication section 40 wirelessly transmits in packets the image data per line. In the present exemplary embodiment, the wireless communication section 40 that performs wireless communication with an external device (here, the control device 12), is adapted to a wireless LAN standard represented by IEEE (Institute of Electrical and Electronics Engineers) 802.11a/b/g/n or the like, and controls the transmission of various types of information between the radiation detection device 14 and the external device by wireless communication.

Further, by communicating through the wireless communication section 40, the control section 36 can wireless communicate with an external device that overall controls radiographic imaging such as the control device 12, and can transmit and receive various types of data to and from the control device 12. When imaging a radiographic image of the subject 19, the control section 36 stores various types of information, such as information of the subject 19 and imaging conditions (imaging menu) received via the wireless communication section 40 from the control device 12, and performs read-out of the charges on the basis of the imaging menu.

The timer 42 has the function of counting the charge accumulation period of the TFT section 30, and a period until the radiation exposure dose exceeds a threshold value (details described below).

In this way, in the radiation detection device 14 of the present exemplary embodiment, a radiographic image corresponding to irradiated radiation is imaged. The operation of imaging a radiographic image, by the radiation detection device 14 of the present exemplary embodiment, is executed without receiving an instruction to image a radiographic image from the control device 12, and without having to synchronize with the irradiation of the radiation by the radiation generation device 16 (details described below).

The radiation detection device 14 of the present exemplary embodiment is equipped with the power source section 48. Each of the sections and so forth described above operates on electrical power supplied from the power source section 48. The power source section 48 has a built-in battery (a rechargeable secondary battery) so as to not impair the portability of the radiation detection device 14, and the power source section 48 supplies the electrical power to the sections and so forth from the charged battery. In FIG. 3, illustration of wires that connects the sections and so forth to the power source section 48 is omitted in order to prevent the drawing from becoming complicated.

Next, a processing (hereinafter called false image output suppression processing) operation in which the radiation detection device 14 of the present exemplary embodiment determines, based on the dose of radiation to which the radiation detection device 14 has been irradiated, whether a radiographic image that has been imaged is a valid image and, when the radiographic image is not a valid image (is a false image), controls the wireless communication section 40 not to output the radiographic image, will be described in detail with reference to the drawings. FIG. 6 is a flowchart showing an example of a flow of the false image output suppression processing that is executed in the radiation detection device 14. When performing the false image output suppression processing, in the control section 36, a pre-stored program stored in a predetermined region of the memory 36B is executed by the CPU 36A.

In step 100, the radiation detection device 14 moves to a radiation detecting mode (radiographic imaging mode). In the radiation detection device 14 of the present exemplary embodiment, when a predetermined detection start condition is met, the radiation detection device 14 is moved by the control section 36 to the radiation detecting mode, in which the radiation detection device 14 detects the radiation irradiated thereto. Examples of the predetermined detection start condition include, when an imaging menu has been registered, when the power has been turned on by the power source section 48, or the like. However, the predetermined detection start condition is not limited thereto.

Then, in the next step 102, the radiation detection device 14 starts detecting the dose of the irradiated radiation. In the radiation detection device 14 of the present exemplary embodiment, the radiation detection device 14 uses a QL value (read value of radiographic image information) to detect the dose of the irradiated radiation. However, the radiation detection method of the radiation detection device 14 is not limited thereto, and may also be configured to use, for example, the charge storage quantity in the TFT section 30 to detect the dose of the irradiated radiation.

In the next step 104, the radiation detection device 14 executes offset image acquisition processing. Note that noise (offset components), such as dark current, may be superimposed on the image data of the radiographic image in which the subject 19 has been imaged (hereinafter called subject image data). Accordingly, in the radiation detection device 14 of the present exemplary embodiment, in order to remove the noise from the subject image data, the radiation detection device 14 executes offset image acquisition processing. This offset image acquisition processing acquires image data (hereinafter called offset image data) for correcting the subject image data, before imaging the subject 19. In the offset image acquisition processing, the radiation detection device 14 performs a reset operation that discharges the charges accumulated in the TFT section 30 at this point in time and then performs imaging in a predetermined period (e.g., a charge storage period instructed from the control device 12) to acquire the offset image data. The offset image data that have been acquired by the offset image acquisition processing are outputted to the control device 12 and are also stored in the storage section 44.

In the next step 106, the radiation detection device 14 determines whether the dose of radiation detected, when executing the offset image acquisition processing, is equal to or greater than a predetermined threshold value. The dose of radiation may be the dose of radiation that predetermined section of pixels have detected, may be doses of radiation that plural pixels have detected, or may be the average value of the doses of radiation.

In the radiographic imaging system 10 of the present exemplary embodiment, a range of doses of radiation detected by the radiation detection device 14 when imaging valid radiographic images (particularly in the present exemplary embodiment, doses of radiation detected by the radiation detection device 14 to which the radiation detection device 14 is irradiated while the offset image acquisition processing) is obtained beforehand. Consequently, detected dose of radiation not within the range represents that the valid radiographic image may not be imaged. In the present exemplary embodiment, the lower limit value of the range of the doses of radiation is predetermined as the threshold value. Accordingly, the radiation detection device 14 is configured to determine that it is not imaging a valid radiographic image (miss-detection) when the detected dose of radiation is less than the threshold value. The setting of the threshold value is not limited thereto and, for example, both the upper limit value and the lower limit value of the range of the doses of radiation may also be set as threshold values. When the detected dose of radiation is less than the threshold value, a negative determination is made in step 106 and the radiation detection device 14 proceeds to step 110. On the other hand, when the detected dose of radiation is equal to or greater than the threshold value, an affirmative determination is made in step 106 and the radiation detection device 14 proceeds to step 108.

In step 108, the radiation detection device 14 acquires from the timer 42 a period representing the time from when the radiation detection device 14 starts detecting the dose of radiation until the detected dose of radiation reaches the threshold value. Then, the radiation detection device 14 determines whether the period is equal to or less than a predetermined period. In the radiographic imaging system 10, the period until the detected dose of radiation by radiation detection device 14 reaches the threshold value, when imaging a valid radiographic image, is obtained beforehand. Consequently, even when the detected dose of radiation has exceeded the threshold value, and when the period has exceeded, this means that the valid radiographic image will not be imaged. Accordingly, in the radiation detection device 14 of the present exemplary embodiment, the timer 42 counts the period from when the radiation detection device 14 starts detecting the dose of radiation until the detected dose of radiation reaches the threshold value.

When the period exceeds the predetermined period, a negative determination is made in step 108, and the radiation detection device 14 proceeds to step 110. In step 110, the radiation detection device 14 determines that the radiographic image obtained by imaging processing is not a valid image, and that the radiation detection device 14 is miss-detecting, stores an indication of miss-detection in the storage section 36C of the control section 36, and proceeds to step 114.

On the other hand, when the amount of arrival time is equal to or less than the predetermined period in step 108, an affirmative determination is made in step 108 and the radiation detection device 14 proceeds to step 112. In step 112, the radiation detection device 14 determines that the radiographic image obtained by imaging processing is the valid image, stores an indication representing that the valid image has been imaged in the storage section 36C of the control section 36, and proceeds to step 114.

In the radiographic imaging system 10 of the present exemplary embodiment, the radiation detection device 14 images the radiographic image without having to synchronize with the radiation irradiation operation of the radiation generation device 16. An example method for performing imaging in such way includes, predetermining a condition for starting charge storage in the TFT section 30, and using the materialization of this condition as a trigger to determine the imaging timing to perform imaging (charge storage). Further, another example method for performing imaging in such way includes, reading out the charges accumulated in predetermined pixels or dedicated pixels, and using the timing when the value of the charges that have been read out exceeds a predetermined threshold value, as an imaging timing to perform imaging. However, the present invention is not limited thereto. Whatever the method, it is preferred that the radiation detection device 14 perform a reset operation that resets the charges that have been accumulated until immediately before starting charge accumulation for imaging a radiographic image. Therefore, in step 114, the radiation detection device 14 performs a reset operation.

Next, in the step 116, the radiation detection device 14 images a radiographic image to acquire the subject image data by radiographic imaging processing that images a radiographic image corresponding to the radiation that has been irradiated, as described above.

Next, in the step 118, the radiation detection device 14 references the storage section 36C to determine whether the imaged radiographic image is a valid image. When the imaged radiographic image is a valid image, the radiation detection device 14 proceeds to step 120. In step 120, the acquired subject image data is output to the control device 12 via the wireless communication section 40. Thereafter, the radiation detection device 14 ends the present processing. On the other hand, when the imaged radiographic image is not a valid image, the radiation detection device 14 ends the present processing without outputting the subject image data to the control device 12. As a configuration to control the radiation detection device 14 not to output the subject image data to the control device 12, the radiation detection device 14 may be configured to transmit the subject image data to the wireless communication section 40 only when the radiation detection device 14 has determined that the radiographic image is a valid image. The radiation detection device 14 may also be configured to transmit the subject image data to the wireless communication section 40 regardless of whether the radiographic image is a valid image and, when the radiographic image is not a valid image, instruct the wireless communication section 40 not to output the subject image data that have been transmitted to the wireless communication section 40.

Subject image data that have been determined to be not a valid image may be disposed of or may be stored in the storage section 44 together with the indication that the subject image data are not valid. Further, when not valid subject image data have been disposed, the indication that not the valid image has been imaged may be stored in the storage section 44.

In the present exemplary embodiment, the wireless communication section 40 does not output anything to the control device 12 when the radiation detection device 14 has determined that the radiographic image is not the valid image, but the wireless communication section 40 may also be configured to output to the control device 12 the indication that not the valid image has been imaged.

As described above, the radiation detection device 14 of the radiographic imaging system 10 according to the present exemplary embodiment, without having to synchronize with the radiation irradiation operation of the radiation generation device 16, detects the dose of the irradiated radiation that has been irradiated from the radiation generation device 16 when acquiring the offset image data, determines, by the control section 36, that the imaged radiographic image is not the valid image when the detected dose of radiation is less than the threshold value or when the detected dose of radiation is equal to or greater than the threshold value and the period until the detected dose of radiation reaches the threshold value exceeds the predetermined period, and controls, by the control section 36, the wireless communication section 40 not to output the radiographic image (subject image data) to the control device 12.

When the detected dose of radiation is equal to or greater than the threshold value and when the period in which the detected dose of radiation reaches the threshold value is equal to or less than the predetermined period, the control section 36 determines that the imaged radiographic is a valid image and instructs the wireless communication section 40 to output the radiographic image (subject image data) to the control device 12.

In this way, in the radiation detection device 14 of the present exemplary embodiment, a false radiographic image that is not valid image may be prevented from being outputted.

In the radiographic imaging system 10 of the present exemplary embodiment, when at least one of the plural radiation detection devices 14 (14₁ to 14n), equipped in the radiographic imaging system 10, images a radiographic image of the subject 19, the false image output suppression processing is executed in all of the radiation detection devices 14 that have detected the radiation. Accordingly, even when one of radiation detection devices 14 has miss-detected the radiation, the imaged radiographic image is not outputted from the radiation detection device 14 that has miss-detected. Accordingly, the radiation detection devices 14 can determine whether the radiographic images are the valid radiographic images, and the control device 12 may only receive the valid radiographic image, since the false radiographic image is not outputted.

Consequently, in the radiographic imaging system 10, the processing time of the workflow from when radiographic imaging is started until the completion of output of the imaged valid image (namely, until the reception of the valid image by the control device 12 is completed) may be shortened, and therefore the convenience may improve. Further, the control device 12 receives only a valid image, and therefore speed for displaying the image in the control device 12 may be prevented from becoming slow.

Further, in the present embodiment, even when the radiographic imaging system 10 is equipped with plural radiation detection devices 14, it is not necessary to select and designate the radiation detection device 14 to image the radiographic image beforehand, and may acquire a valid radiographic image. Accordingly, in the present embodiment, there is no worry of mistaking in the selection and designation of the radiation detection device 14. Consequently, re-imaging due to the mistake may be prevented, and the subject 19 may be prevented from being needlessly irradiated by the radiation.

Further, the radiation detection device 14 of the present exemplary embodiment determines whether the radiographic image is valid on the basis of the detected dose of radiation. Accordingly, the present invention may perform processing more quickly than performing an image analysis and performing a determination as in the conventional technology.

In the present exemplary embodiment, the radiation detection device 14 determines whether the imaged radiographic image is a valid image on the basis of the detected dose of radiation while the offset image acquisition processing in which the radiation detection device 14 acquires the offset image data. However, the present invention is not limited thereto. The radiation detection device 14 may also be configured to determine whether the imaged radiographic image is a valid image on the basis of the detected dose of radiation while the radiographic imaging processing in which the radiation detection device 14 acquires the subject image data.

Further, in the present exemplary embodiment, the radiation detection device 14 performs the radiographic imaging processing after determining whether the imaged radiographic image is a valid image on the basis of the detected dose of radiation while the offset image acquisition processing in which the radiation detection device 14 acquires the offset image data. However, the present invention is not limited thereto. The radiation detection device 14 may also be configured not to perform the imaging processing when it has determined that the imaged radiographic image is not the valid image.

Further, the radiographic imaging system 10 of the present exemplary embodiment is configured to have more than one of the radiation detection devices 14. However, the present invention is not limited thereto. The radiographic imaging system 10 may also be configured to have one radiation detection device 14. Even in such case, a radiographic image that has been imaged can be prevented from being outputted to the control device 12 when imaging of the subject 19 could not be validly performed. Consequently, for example, user convenience may be improved.

Further, the configurations and so forth of the radiographic imaging system 10, the control device 12, the radiation detection device 14, and the radiation generation device 16 and the like, described in the present exemplary embodiment are examples and are capable of being modified and changed depending on the situation within a scope not departing from the gist of the present invention.

Further, the example of the flow of the false image output suppression processing described in the present exemplary embodiment (FIG. 6) is also an example, and may be modified or changed depending on the situation within a scope not departing from the gist of the present invention.

Further, in the present exemplary embodiment, a case in which X-rays are irradiated as the radiation, has been described. However, the present invention is not limited thereto. Gamma rays or the like may also be irradiated.

What is claimed is:

1. A radiographic imaging device, comprising:
   a detecting section that detects a dose of radiation that has been irradiated, in a case in which a radiographic image corresponding to irradiated radiation is imaged;
   an image acquisition section that acquires the radiographic image;
   a storage section that stores the radiographic image; and
   a control section that, in a case in which a determination is made such that a timing for imaging the radiographic image has been falsely detected on the basis of the dose of radiation that has been detected by the detecting section, performs control so as to dispose of the radiographic image acquired by the image acquisition section, or to store the acquired radiographic image at the storage section together with information indicating that the radiographic image was imaged with a false detection; wherein
   the control section does not determine that a false detection has been made in a case in which the dose of radiation detected by the detecting section reaches a predetermined threshold value within a predetermined period from commencement of detection of the dose of radiation.

2. The radiographic imaging device according to claim 1, wherein the control section determines that a false detection has been made in at least one selected from the group consisting of a case in which the dose of radiation detected by the detecting section does not reach a predetermined threshold value, and a case in which the dose of radiation does not reach a predetermined threshold value within a predetermined period from commencement of detection of the dose of radiation.

3. The radiographic imaging device according to claim 1, further comprising a battery that supplies electrical power to the detecting section, the image acquisition section, the storage section, and the control section.

4. The radiographic imaging device according to claim 3, wherein the battery is a rechargeable battery.

5. The radiographic imaging device according to claim 1, wherein:
   the storage section stores a plurality of the radiographic images; and
   the control section controls the storage section so as to sequentially store the radiographic images, in a case in which the radiographic images acquired by the image acquisition section are stored in the storage section.

6. The radiographic imaging device according to claim 1, wherein the control section outputs information that indicates a determination result, in a case in which the control section determines that a false detection has been made.

7. The radiographic imaging device according to claim 1, wherein the control section determines whether or not a false detection has been made on the basis of the dose of radiation that has been detected by the detecting section in a case in which a subject for the radiographic image is imaged.

8. The radiographic imaging device according to claim 1, wherein the control section determines whether or not a false detection has been made based on the dose of radiation detected by the detecting section in a case in which an offset image is acquired.

9. The radiographic imaging device according to claim 1, further comprising a wireless communication section that receives imaging conditions.

10. A radiographic imaging system, comprising:
    a control device that instructs settings related to imaging a radiographic image;
    a radiation irradiation device that irradiates radiation on the basis of an instruction from the control device; and
    the radiographic imaging device according to claim 1 which, without having to synchronize with an operation of irradiation of the radiation by the radiation irradiation device, images a radiographic image corresponding to the radiation that has been irradiated from the radiation irradiation device, and outputs the imaged radiographic image to the control device.

11. The radiographic imaging system according to claim 10, wherein the radiographic imaging system includes a plurality of the radiographic imaging devices.

12. A non-transitory computer-readable medium storing a radiographic imaging program executable by a computer to function as the control section of the radiographic imaging device according to claim 1.

13. A radiographic imaging method, comprising:
    detecting, by the detecting section of the radiographic imaging device according to claim 1, a dose of radiation that has been irradiated;
    acquiring, by the image acquisition section of the radiographic imaging device according to claim 1, the radiographic image; and
    controlling, by the control section of the radiographic imaging device according to claim 1, in a case in which a determination is made such that a timing for imaging the radiographic image has been falsely detected on the basis of the dose of radiation that has been detected by the detecting section, so as to dispose of the radiographic image acquired by the image acquisition section, or to store the acquired radiographic image at the storage section together with information indicating that the radiographic image was imaged with a false detection.

* * * * *